(12) United States Patent
Goto et al.

(10) Patent No.: US 9,314,774 B2
(45) Date of Patent: Apr. 19, 2016

(54) CATALYST FOR METHANOL PRODUCTION, METHOD OF PRODUCING THE SAME AND PROCESS OF METHANOL PRODUCTION

(71) Applicant: MITSUI CHEMICALS, INC., Tokyo (JP)

(72) Inventors: Yuya Goto, Chiba (JP); Naoya Takahashi, Sodegaura (JP); Masaki Yoshinaga, Nagoya (JP); Masami Murakami, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/404,166

(22) PCT Filed: Jun. 3, 2013

(86) PCT No.: PCT/JP2013/065325
§ 371 (c)(1),
(2) Date: Nov. 26, 2014

(87) PCT Pub. No.: WO2013/183577
PCT Pub. Date: Dec. 12, 2013

(65) Prior Publication Data
US 2015/0111975 A1 Apr. 23, 2015

(30) Foreign Application Priority Data
Jun. 4, 2012 (JP) .................................. 2012-127031

(51) Int. Cl.
*B01J 21/08* (2006.01)
*C07C 27/00* (2006.01)
*B01J 23/80* (2006.01)
*C07C 29/154* (2006.01)
*B01J 37/03* (2006.01)
*B01J 35/00* (2006.01)
*B01J 35/10* (2006.01)
*B01J 37/08* (2006.01)

(52) U.S. Cl.
CPC ............... *B01J 23/80* (2013.01); *B01J 35/002* (2013.01); *B01J 35/1014* (2013.01); *B01J 37/031* (2013.01); *B01J 37/08* (2013.01); *C07C 29/154* (2013.01); *B01J 2523/00* (2013.01); *Y02P 20/52* (2015.11)

(58) Field of Classification Search
CPC .... B01J 23/80; B01J 2523/41; B01J 2523/31; B01J 2523/27; B01J 2523/17; C07C 31/04
USPC .................. 502/244, 250, 342, 343, 345, 346
See application file for complete search history.

(56) References Cited

U.S. PATENT DOCUMENTS

| 5,767,039 A * | 6/1998 | Yamagishi ............... B01J 23/80 |
| | | 502/342 |
| 6,048,820 A | 4/2000 | Matsuda |
| 2011/0301022 A1 | 12/2011 | Murakami |

FOREIGN PATENT DOCUMENTS

| CN | 101306369 | 11/2008 |
| CN | 102302934 | 1/2012 |
| JP | S63039287 | 8/1988 |
| JP | H06312138 | 11/1994 |
| JP | H07039755 | 2/1995 |
| JP | 3-299796 | 11/1996 |
| JP | H10309466 | 11/1998 |
| JP | 2010194419 A2 | 9/2010 |
| JP | 2010194420 A2 | 9/2010 |
| JP | 2010194421 A2 | 9/2010 |
| WO | 2011048976 A1 | 4/2011 |

OTHER PUBLICATIONS

Jiang et al, Microstructural evolution, microhardness and thermal stability of HPT processed Cu, (Material Science and Engineering A 290 (2000) 128-138).*
International Search Report dated Jul. 9, 2013 filed in PCT/JP2013/065325.
"Shokubai Koza (Lectures of Catalysts)," Catalyst study, vol. 7 edited by Catalyst Scientific Society issued by Kodansha Ltd., on Jul. 20, 1989, pp. 21-39; Partial English translation thereof; Cited in Specification.
M. Saito et al., "Development of copper/zinc oxide-based multicomponent catalysts for methanol synthesis from carbon dioxide and hydrogen," Applied Catalysis A: General, 138, 1996, pp. 311-318; Cited in Specification.
M. P. Luna et al., Reaccion De Gas De Sintesis Con Catalizadores De Si-Al-Zn-M (M=Cu, Co, Th, Mn y Mo), Revista Del Instituto Mexicano Del Petroleo, vol. 25, 1993, pp. 60-66.; Cited in International Search Report.
H. Wei et al., "Effect of Si/Al ratio on the performance of Cu-Zn-Si-Al catalyst prepared by complete liquid-phase technology for dimethyl ether syntehsis from syngas," Gaodeng Xuexiao Huaxue Xuebao, vol. 32, 2011, pp. 118-123.; English abstract included; Cited in International Search Report.
K.-W. Jun et al., "Residual sodium effect on the catalytic activity of Cu/ZnO/Al2O3 in methanol synthesis from CO2 hydrogenation," Applied Catalysis A: General, vol. 174, 1998, pp. 231-238.; Cited in International Search Report.
Japanese Office Action dated Sep. 15, 2015 issued in the corresponding Japanese patent application No. 2014-519976.
Extended European Search Report dated Jan. 14, 2016 issued in the corresponding European patent application No. 13800704.2.

* cited by examiner

Primary Examiner — Jafar Parsa
(74) Attorney, Agent, or Firm — Rankin, Hill & Clark LLP (57) ABSTRACT

[Problem] The present invention is to provide a catalyst used for a process for preparing methanol from carbon dioxide and hydrogen and the catalyst has high activity and excellent stability with the passage of time in reactivity.
[Solution] The catalyst comprises copper, zinc, aluminum and silicon, and has a molar ratio of zinc to copper of 0.5 to 0.7, a molar ratio of silicon to copper of 0.015 to 0.05, a maximum intensity ratio of a peak derived from zinc to a peak derived from copper of not more than 0.25 and a half-value width (2θ) of the peak derived from copper of 0.75 to 2.5. The process for producing methanol comprises using the catalyst.

14 Claims, 2 Drawing Sheets

CATALYST FOR METHANOL PRODUCTION, METHOD OF PRODUCING THE SAME AND PROCESS OF METHANOL PRODUCTION

TECHNICAL FIELD

The present invention relates to a copper type catalyst for synthesizing methanol by a reaction of hydrogen and carbon oxides containing carbon dioxide as a main component, and particularly it relates to a method of producing a copper type catalyst having remarkably excellent durability and good catalyst activity and capable of suppressing lowering of catalyst activity caused by water which is formed as a by-product in the case of using carbon dioxide as a reaction substrate.

BACKGROUND ART

A methanol synthesis process is a very important basic process in chemical industries, and the high efficiency on the methanol synthesis process has been constantly demanded from the viewpoint of saving of energy and economic efficiency.

In conventionally known methanol synthesis processes, a synthetic gas (a mixed gas of CO and $H_2$) is used as a main raw material (containing a small amount of $CO_2$) and a three-component type catalyst such as $Cu/ZnO/Al_2O_3$ catalyst (present industrial catalyst, for example Non-patent document 1) and $Cu/ZnO/SiO_2$ catalyst (Patent document 1) is known as its catalyst.

In a conventional methanol synthesis technique using a synthetic gas as a raw material, it is known that the catalyst is stable for a period of several years. In the methanol synthesis using $CO_2$ and $H_2$ as raw materials related to the field of the present invention, the same activity stability of the catalyst has been also desired now but it is difficult to say that the activity stability is sufficient.

Meanwhile, from studies on reuse and recycling of carbon resources in order to decrease GHG (green house effect gas) and on global environment problems, there is increasing interest in a process of methanol synthesis by using $CO_2$ and $H_2$ as main raw materials recently in place of the conventional processes of using a synthetic gas as a main material.

In the methanol synthesis from a raw material gas having a high $CO_2$ content, a catalyst is demanded to have a higher activity than that used in the methanol synthesis from the above synthetic gas for the sake of thermodynamic equilibrium in the reaction and reaction inhibiting effect of water generated together with methanol (Non-patent document 2). Moreover, in the methanol synthesis from a raw material gas having a high $CO_2$ content, the lowering of the catalyst activity, which will be caused by water generated as a by-product together with methanol, is significantly large as compared with the methanol synthesis from a synthetic gas. On this account, the catalyst having a higher durability is demanded as compared with the catalyst used in the methanol synthesis from the synthetic gas. This is considered that the three-component catalyst, which is used in the methanol synthesis from the synthetic gas, does not have sufficient catalyst performance.

Under the circumstances, a copper type multi-component catalyst comprising additional components, such as copper/zinc oxide/aluminum oxide/zirconium oxide, or copper/zinc oxide/aluminum oxide/zirconium oxide/gallium oxide has been developed (for example, Patent documents 2 and 3).

Furthermore, a catalyst having high activity prepared by adding colloidal silica or a water solved silica in an amount of 0.3 to 0.9 wt % as silica and calcination at a temperature of 480 to 690° C. has been developed (Patent document 4).

The present applicant discloses preferable methods of producing these copper type catalysts (Patent documents 5, 6 and 7).

CITATION LIST

Patent Document

Patent document 1: JP-B-S63(1988)-39287
Patent document 2: JP-A-H7(1995;-39755
Patent document 3: JP-A-H6(1994;-312138
Patent document 4: JP-A-H10(1998)-309466
Patent document 5: JP-A-2010-194419
Patent document 6: JP-A-2010-194420
Patent document 7: JP-A-2010-194421

Non-Patent Document

Non-patent document 1: Catalyst study, Vol. 7 edited by Catalyst Scientific Society issued by Kodansha Co., on Jul. 20, 1989, pp. 21-39
Non-patent document 2: Applied Catalysis A: General, 38(1996) pp. 311-318

SUMMARY OF INVENTION

Problems to be Solved by the Invention

It is true that the above-described copper type multi-component catalyst has high activity in an initial stage of the reaction using $CO_2$ and $H_2$ as raw materials. However, according to the studies of the present inventors, it has been clear that the activity tends to be gradually decreased by the influence of water generated as a by-product. Namely, the present inventors found that it is necessary for the catalyst to have higher performances on long-time persistence of reaction and durability.

In conventional methanol synthesis using a synthetic gas as a raw material, it is known that the catalyst is stable for several years. In the methanol synthesis using $CO_2$ and $H_2$ as raw materials related to the present field, the catalyst having the same stability of activity is also tend to be demanded. However, it is difficult to say that the stability of activity of the present catalyst is sufficient under the present situation.

The present invention has been conducted under the circumstances as described above. It is an object of the present invention to provide a catalyst having good catalyst activity and remarkably excellent durability in the methanol synthesis from hydrogen and carbon oxides mainly containing carbon dioxide, and it is another object of the present invention to provide a production method of the catalyst, and it is a further object of the present invention to provide a process for producing methanol using this catalyst.

Problem Solution

The present invention relates to a catalyst for producing methanol, which catalyst comprises metal oxides, particularly composite metal oxides containing copper as a main component, and it relates to a method for producing the catalyst.

Namely, the catalyst of the present invention is a catalyst for methanol production using, as a raw material, carbon oxides and comprises copper, zinc, aluminum and silicon and has the following properties;

(A) the molar ratio of zinc to copper is 0.5 to 0.7,
(B) the molar ratio of silicon to copper is 0.015 to 0.05,
(C) the maximum intensity ratio of a peak derived from zinc to a peak derived from copper, as measured by XRD, is not more than 0.25, and
(D) the half-value width (2θ) of a peak derived from copper, as measured by XRD, is 0.75 to 2.5.

Further, the catalyst for methanol production according to the present invention has the following property;
(E) the content of zirconium is 0 to 0.1 mol %.

Furthermore, the catalyst for methanol production according to the present invention preferably has a content of copper of 45 to 65 mol % provided that the total amount of copper, zinc, aluminum and silicon is 100 mol %, and a content of an alkali metal of 0 to 0.2 mol %.

The catalyst for methanol production according to the present invention is obtainable through a step of calcination at a temperature of 300° C. to 450° C.

Further, the present invention relates to the process for producing methanol using the resultant catalyst for methanol production in the presence of carbon oxides and hydrogen.

Effect of the Invention

The catalyst for methanol production according to the present invention has a high activity in a reaction of carbon dioxide and hydrogen and also retains the high activity for a long period of time. That is to say, the catalyst has excellent durability. On this account, the catalyst can efficiently and stably convert carbon dioxide, which causes the warming of the earth, into a chemical raw material such as methanol. Therefore, it is desired that the catalyst will contribute to the industries and global environment.

EMBODIMENT FOR CARRYING OUT THE INVENTION

The present invention provides a catalyst for methanol production which catalyst comprises a metal oxide having a specific composition and a crystal form and can efficiently produce methanol from hydrogen and carbon oxides such as carbon dioxide, the present invention further provides a method for producing the catalyst and a process for producing methanol using the catalyst.

The present invention will be described in detail below.

<<Catalyst for Methanol Production>>

The catalyst for methanol production according to the present invention is a copper type catalyst and has good catalyst activity in a methanol synthesis reaction from hydrogen and carbon oxides essentially containing carbon dioxide and also has remarkably excellent durability. It is a matter of course that the catalyst has good catalyst activity and remarkably excellent durability even in a methanol synthesis from a synthesized gas and a reverse reaction thereof, a methanol reforming reaction, a shift reaction and a reverse reaction thereof. Moreover, the components of the catalyst for methanol production according to the present invention are not limited to the above-described components and may comprise other oxides.

The catalyst for methanol production according to the present invention comprises copper, zinc, aluminum and silicon as essential components.

In a conventional copper type catalyst, an attempt has been made such that the content of components particularly zinc is specified based on copper contained in the catalyst to prepare a catalyst having high activity. However, an embodiment of enhancing the durability of a catalyst could not be found.

The present inventors have been earnestly studied in order to prepare a catalyst having a low decrease of activity with time in a methanol synthesis reaction, namely having high durability without deterioration, and found that it is very important to control the contents of zinc, aluminum and silicon based on copper and to control the crystal form which can be characterized by XRD measurement.

The catalyst for methanol production according to the present invention is characterized by satisfying the following properties (A) to (D).
(A) The molar ratio of zinc to copper is 0.5 to 0.7,
(B) the molar ratio of silicon to copper is 0.015 to 0.05,
(C) the maximum intensity ratio of a peak derived from zinc to a peak derived from copper, as measured by XRD, is not more than 0.25, and
(D) the half-value width (2θ) of a peak derived from copper, as measured by XRD, is 0.75 to 2.5.

It is considered that the main active component of the catalyst for methanol production according to the present invention is copper. The copper is generally produced as an oxide thereof.

The catalyst for methanol production according to the present invention is mostly used after activating by a highly activating method of reducing copper oxide to copper before the reaction of carbon dioxide and hydrogen or in the initial reaction at a reduction atmosphere.

In order to generally prepare the catalyst having such a high activity, the content of copper is preferably 45 to 65 mol %, more preferably 50 to 65 mol % based on 100 mol % of the total amount of copper, zinc, aluminum and silicon, which are contained in the catalyst.

In this catalyst, copper is generally present as copper oxide and copper oxide is regarded as copper oxide represented by the chemical formula $CuO$. Furthermore, zinc is regarded to be present in the catalyst as zinc oxide represented by the chemical formula $ZnO$. This zinc is considered to be a component capable of highly dispersing copper or highly activating copper by interaction with copper.

The amount of zinc contained in the catalyst for methanol production according to the present invention is determined as the ratio to the amount of copper, and zinc is contained in an amount that the molar ratio of zinc to copper is 0.5 to 0.7, preferably 0.5 to 0.65. When the content of zinc is too large, the content of copper, which is a main catalyst component, is decreased to lower the reaction activity in some cases. On the other hand, when the content of zinc is too small, as described above, aggregation of copper is easily caused and the reaction activity tends to be decreased with time.

In the catalyst for methanol production according to the present invention, the content of zinc is preferably 25 to 46 mol %, more preferably 29 to 40 mol % based on 100 mol % of the total of copper, zinc, aluminum and silicon in order to prepare the catalyst having high activity.

As compared with catalysts prepared by a conventional technique, the catalyst for methanol production according to the present invention has a not so high content of copper, but it shows high activity. It is considered that the ratio of copper and zinc is one reason why the catalyst has high activity.

The silicon contained in the catalyst for methanol production according to the present invention is considered to be substantially present as silicon oxide represented by the chemical formula $SiO_2$ and the molar ratio of silicon to copper is 0.015 to 0.05, preferably 0.015 to 0.045, more preferably 0.020 to 0.045. When silicon satisfies this molar ratio, the lowering of the catalyst activity with time is suppressed and the high activity can be kept stably.

The addition of silicon to the catalyst for methanol production has been conventionally conducted in order to suppress the lowering of the activity, but the effect is not necessarily so high. The present inventors found that the catalyst can have both of high reaction activity and high reaction durability by defining not only the ratio of silicon to copper but also the ratio of zinc to copper.

The content of silicon contained in the catalyst for methanol production according to the present invention is preferably 0.7 to 3.3 mol %, more preferably 0.7 to 3.0 mol %, furthermore preferably 1.0 to 3.0 mol % based on 100 mol % of the total amount of copper, zinc, aluminum and silicon in order that the catalyst has high activity.

The reason why the catalyst for methanol production satisfying such a composition according to the present invention has improved high activity and durability without deterioration is not definite. It is presumed that silicon oxide has some kind of influence on the dispersibility of copper and zinc oxide in a composite thereof and thereby sintering of the composite of copper and zinc oxide is suppressed. Therefore, when the content of silicon is in the above range, reduction of the effect of suppressing sintering due to lack of silicon is not occurred, and inhibition of the reaction at an active site due to an excess amount of silicon is not occurred. Accordingly, it is presumed that the catalyst has high activity and high durability.

The catalyst for methanol production according to the present invention has a maximum intensity ratio of a peak derived from zinc to a peak derived from copper, as determined by XRD measurement, of not more than 0.25. Namely, this ratio indicates that the peak derived from zinc is relatively smaller as compared with the peak derived from copper. This fact indicates that the content of crystallization of zinc oxide is small, and it is considered that zinc oxide is present in a state of fine particles.

The catalyst having these properties efficiently exerts interaction between copper, which is an active species, and zinc oxide and it is considered that the improvement of reaction activity and the suppression of copper aggregation are revealed efficiently. Moreover, when the catalyst contains silicon in a specific amount, it is presumed that sintering of zinc oxide is suppressed and the above specific effect can be revealed.

Aluminum is also an essential component of the catalyst for methanol production according to the present invention, and it is probably considered that aluminum contributes enlarging the surface area of copper and zinc oxide. Aluminum is generally present as aluminum oxide in the catalyst, and it is considered that aluminum oxide, as it is, does not have activity for the present reaction. Therefore, the aluminum content may have a sufficient effect so as to enlarge the surface area of copper and zinc oxide. When the aluminum content is larger than the necessary content thereof, the catalyst activity is sometimes lowered.

In the present invention, the catalyst contains aluminum in an amount of preferably 1 to 12 mol %, more preferably 1 to 10 mol %, furthermore preferably 1 to 8 mol %, particularly preferably 2 to 6 mol % based on 100 mol % of the total amount of copper, zinc, aluminum and silicon. The aluminum oxide expressed herein is substantially regarded as a compound represented by the chemical formula $Al_2O_3$.

For the catalyst for methanol production according to the present invention, the effect of containing zirconium oxide is not necessarily so high. Zirconium is preferably contained for suppressing sintering, because it is presumed that the components such as copper are hardly crystallized. While, it will give rise to adverse effects such that the change of the crystal structure necessary for high activation is suppressed. When the zirconium content is too large, it is necessary to conduct calcination at a high temperature in order to enhance the activity. However, when the calcination at a high temperature is conducted, it is presumed that unnecessary crystal growth will be easily occurred.

The content of zirconium in the catalyst for methanol production according to the present invention is preferably 0 to 0.1 mol % based on 100 mol % of the total amount of copper, zinc, aluminum and silicon.

The content of an alkali metal in the catalyst for methanol production according to the present invention is preferably 0 to 0.2 mol % based on 100 mol % of the total amount of copper, zinc, aluminum and silicon. When the content of the alkali metal is in the above range, there is a tendency that good catalyst activity is revealed without acceleration of catalyst sintering.

The catalyst for methanol production according to the present invention may include other metal oxides in addition to the above essential components except for an alkali metal. For example, Group 2 to 15 metals in the Periodic Table, such as gallium oxide can be added optionally as long as it is not contrary to the object of the present invention. However, it is preferred to avoid zirconium as described above.

When the catalyst for methanol production according to the present invention has the above-described appropriate catalyst composition, it has high catalyst performances such as high activity and high durability by determining the appropriate reaction conditions in accordance with the objective reaction, and particularly it has the high catalyst performances in the methanol synthesis by a reaction of hydrogen and carbon oxides principally containing carbon dioxide.

<<Method of Producing the Catalyst for Methanol Production>>

Production of Catalyst Precursor

As the method of producing the catalyst for methanol production according to the present invention, a known method can be used without limitation as long as it satisfies the above requirements. Specifically, it is preferred that a method can highly disperse various kinds of constitutional components. As a simple and easy method, there is a well-known method such that a catalyst precursor, which principally comprises a carbonate or hydroxide obtainable by generating precipitation in a solution, is formed and then this catalyst precursor is washed and calcined to prepare an oxide.

The method for producing the catalyst precursor said herein comprises a step, which largely influence on catalyst performances in the production method of the catalyst having an appropriate composition for methanol production. Particularly, it is preferred to produce the catalyst precursor that catalyst components in particles formed by precipitation are dispersed uniformly because the catalyst easily has high activity.

The catalyst precursor according to the present invention is preferably obtainable by precipitation using the two kinds of solutions as described later. Examples of the raw material include an acidic metal salt. The essential metals are copper and zinc, and in addition to the essential metals, Group 2 to 15 metals in the Periodic Table may be contained. As described above, it is preferred to avoid zirconium.

The acidic metal salt is usually at least one selected from a nitrate, a chloride, a sulfate, a carbonate and an oxalate of the metal.

In the catalyst for methanol production according to the present invention, aluminum, which is an essential component, may be also derived from the above-described acidic metal salt, or may be particles of aluminum hydroxide or aluminum oxide.

In the catalyst for methanol production according to the present invention, silicon, which is an essential component, is generally present as an oxide. Examples of the raw material thereof include preferably colloidal silica and silica dissolved in water. Furthermore, colloidal silica and silica dissolved in water may be used together. When silica dissolved in water is used, natural fresh water, tap water, well water or industrial water can be used as water.

In general, the catalyst precursor is preferably produced by a method such that an A solution which comprises an aqueous solution of the metal component acidic water soluble salt and a B solution which comprises an aqueous solution of a precipitating agent are mixed and a precipitate is formed because the metal components are dispersed uniformly.

A basic compound used in the precipitating agent constituting the B solution comprises at least one selected from a carbonate and a hydroxide of an alkali metal containing at least one of lithium, sodium, calcium, rubidium and cesium, and ammonia.

In forming the precipitate by mixing the A solution and the B solution, examples of a precipitating method are:

(1) a method of putting the A solution in a precipitation tank previously and then putting the B solution in the tank;
(2) a method of conversely putting the B solution in a precipitation tank previously and then putting the A solution in the tank;
(3) a method of batch mixing the A solution and the B solution in a precipitation tank; and
(4) A method of dividing the A solution into 2 or more, mixing the A solution containing one or two or more of the metal compounds with the B solution, forming a precipitate and adding the other A solution containing the residue components of the metal compound into the solution containing the precipitate and thereby forming a precipitate.

In addition to the above methods, various methods can be employed appropriately. For the sake of dispersing each component uniformly, preferable is a method in which sufficient stirring is carried out in an appropriate concentration of metal component and a precipitating agent in order to progress the precipitating reaction quickly. The catalyst precursor is formed at a temperature of preferably 10 to 70° C. When the temperature is higher than 10° C., the precipitating forming reaction has a tendency to progress quickly. Moreover, the temperature is preferably not higher than 70° C., because the formed precipitate easily keeps a stable structure containing hydroxide as a main component.

The precipitation time is preferably 10 to 180 min, but it can be shorter than the above time as long as the stirring is carried out sufficiently. Precipitation time longer than the above time is uneconomical, and in the case of carrying out precipitation forming by previously putting one of the A solution and the B solution in the precipitation tank and then feeding the other, it causes continuous change of pH for a long period of time and thereby the crystal structure may be affected and lead to non-uniform structure. In the present invention, in order to control the crystal structure, it is preferred that precipitation forming is carried out quickly as much as possible and the pH at the completion of the precipitation is the same as initial pH of the precipitation. It is preferable for producing a highly active catalyst that catalyst aging is appropriately carried out starting at this pH and thereby the crystal structure of the precursor is easily stabilized.

With regard to the A solution and the B solution, the the upper limits of the metal component concentration in the aqueous solution and the precipitating agent concentration are not particularly limited as long as for the A solution, the acidic metal salt can be completely dissolved, and for the B solution, the precipitating agent can be completely dissolved and stirring can be conducted sufficiently. Moreover, the lower limits thereof are not limited particularly. However, it is preferred to select the concentration in consideration of economical efficiency because too low concentration would lead to remarkable decrease in the production efficiency.

The shape of the precipitation tank is not particularly limited, and it is preferred to be cylindrical in order that the solution is stirred uniformly during the period of precipitation forming. In the precipitation tank, a baffle plate may be set appropriately in order to conduct stirring efficiently. With regard to the method of stirring the solution, the stirring is generally carried out by putting stirring blades in the solution and rotating the blades by means of a stirring motor, and further the stirring effect may be attained by sucking the solution by means of a pump forcedly, blowing it into the precipitation tank and thereby circulating the solution without the use of stirring blades.

After the completion of the precipitation formation of the catalyst precursor by feeding the A solution or the B solution, or the both of them, aging is appropriately conducted in order to control the crystal structure. This aging is generally conducted in such a way that the precipitation solution is in the same precipitation tank or the precipitation solution is transferred to another vessel. The temperature of the aging relates to the time of controlling the structure. The higher the temperature is, the shorter the time is needed to control to the desired structure. However, when the temperature is too high, the crystal structure is changed rapidly and thereby it is difficult to control the crystal structure.

In the present invention, the aging temperature is 35 to 95° C., preferably 45 to 90° C., more preferably 50 to 85° C. The higher the temperature is, the shorter the aging time is needed. The aging is preferably ended up before the surface area of the catalyst precursor is reduced. This time is more or less influenced by the composition. In the composition of the present invention, if the time is within about 24 hr, it may be left out of consideration.

The relative proportion of copper, zinc, silicon and aluminum contained in the A solution does not change after they are made into a solid catalyst through the washing step and the calcination step as described later.

Washing of Catalyst Precursor

The catalyst precursor prepared through the aging step is washed with water appropriately to remove the precipitating agent. In particular, when the alkali metal salt is used as the precipitating agent, it is apt to remain in the catalyst precursor. As described above, as the presence of the alkali metal in the catalyst sometimes decrease the activity considerably in the methanol synthesis reaction, the alkali metal is desirably removed as much as possible. In the present invention, the content of the alkali metal is preferably not more than 0.2 mol % based on 100 mol % of the total amount of copper, zinc, aluminum and silicon.

The method of washing for the removal of the precipitating agent is not particularly limited. Various washing methods may be used. For example, there are a general method of filtration while washing and a method of making a cake by filtration, dispersing it in water again and then filtering repeatedly. It is preferred to form the washed catalyst precursor into a cake state finally by removing moisture with filtration or the like as much as possible.

Calcination of Catalyst Precursor

Normally, the cake-like catalyst precursor is appropriately dried and then calcined to prepare the catalyst. Before the drying, it is preferred to loosen the cake in order that moisture easily comes out. Although the drying conditions are not limited particularly, the drying is carried out in the air at a temperature of 80 to 150° C.

The calcination is carried out in order to make the components of the catalyst precursor into oxides mainly. In order to prepare the catalyst for methanol production according to the present invention, the calcination temperature is preferably from 300 to 450° C., more preferably 350 to 450° C. In the case of using the catalyst precursor as the high-active catalyst to the methanol synthesis reaction, the calcination is preferably carried out until the peak derived from the precursor is not observed by XRD measurement.

The copper oxide in the catalyst for methanol production according to the present invention desirably has a certain level of crystallinity in order that it is stably present in the catalyst. When the crystallinity is too low, rapid sintering occurs because copper particles reduced in the methanol synthesis reaction are too small, and thereby the active site is decreased remarkably and the performance is lowered. While when the crystallization is progressed excessively in the calcination, the stability is high but the active site is apt to decrease remarkably.

The catalyst for methanol production according to the present invention has a half value width ($2\theta$) of the copper peak of from 0.75 to 2.5. The lower limit is preferably 0.80, more preferably 0.85. The upper limit is preferably 2.3, more preferably 2.1.

Probably, in the catalyst satisfying the above range, since copper is interacted with zinc, silicon or aluminum and further, the copper component has a highly stable crystal form, the copper is highly dispersed therein and the catalyst has activity stable with time. The present invention has been accomplished by finding the catalyst capable of realizing such specific performances.

In the catalyst for methanol production according to the present invention, the key factor of controlling the peak intensity ratio of zinc to copper and the half value width of the peak of copper in the above preferred ranges as measured by XRD is the calcination temperature. When the calcination temperature is too high, the crystallization of zinc or copper proceeds to excess and the peak intensity and the half-value width are apt to fall outside the preferred ranges. For example, the peak intensity of copper may be too high or the half-value width of copper peak may be too small. When the calcination temperature is too low, the oxidation reaction hardly proceeds and thereby the catalyst having excellent activity and durability cannot be obtained or the reaction needs many hours.

The catalyst for methanol production obtainable by the above-described method according to the present invention is usually prepared in a powdery state. Accordingly, the catalyst in a powdery state may be used as it is. In the industrial use, the catalyst is usually made into a tablet by extrusion molding or compression molding. The size and the shape of the catalyst in a tablet are not particularly limited. The catalyst thus formed is usually packed in a reactor and used.

In the present invention, the contents of each of copper, zinc, aluminum, silicon, zirconium and an alkali metal in the precursor of the catalyst for methanol production are substantially the same as those in the catalyst described later. In the calcination step, the disappearance of each of the elements is not caused substantially.

The contents of various elements can be determined by the above preparation ratio. Furthermore, the contents can be also determined by measuring the precursor or the catalyst with a conventionally known method such as an atomic absorption spectrometry (AAS) or an inductively coupled plasma atomic emission spectrometry (ICP-AES).

Crystal Structure Analysis by XRD

The analysis of the crystal structure of the catalyst for methanol production according to the present invention was carried out by XRD measurement in the following method.

Powder X-ray diffraction device: Multi Flex manufactured by Rigaku Corporation
[Device Conditions]
X-ray: CuK$\alpha$, 40 kV-40 mA
Goniometer: Multi Flex goniometer (without shutter)
Attachment: a holder for a standard specimen
Counter monochrometer: fixed monochrometer
Counter: Scintillation counter
Divergent slit: 1°
Scattering slit: 1°
Light receiving slit: 0.30 mm(1) or 0.15 mm(2) is selected appropriately.
Monochromatic light receiving slit: none
[Measuring Conditions]
Operation mode: continuous
Sampling width: 0.020° (1) or 0.10° (2) is selected appropriately.
Operation axis: $2\theta/\theta$
Scanning speed: 0.5°/min
Measurement range: $10°\leq 2\theta \leq 80°$ (1) or $25°\leq 2\theta \leq 45°$ (2) is selected appropriately.
Cumulative Number: 2

In the present invention, the intensity ratio of the peak derived from zinc and the peak derived from copper, and the half-value width of the peak derived from copper are determined based on the results measured in the above conditions.

Function

The XRD measurement results indicate that copper, zinc, aluminum and silicon are usually present in a copper oxide, a zinc oxide, an aluminum oxide and a silicon oxide in the catalyst for methanol production according to the present invention, the uniformity thereof is high and copper and zinc are highly dispersed therein. On this account, the catalyst for methanol production according to the present invention has high activity and excellent durability capable of having the high activity for a long period of time.

<<Process for Producing Methanol>>

The catalyst for methanol production according to the present invention is used in a reaction in accordance with the purpose thereof and particularly it is useful in a reaction of synthesizing methanol from hydrogen and carbon oxides ($CO_2$ alone or a mixed gas of $CO_2$ and CO), or a reverse reaction thereof.

The catalyst for methanol production according to the present invention may be used as it is in the production of methanol. It is usual to reduce the catalyst by a reducing gas such as $H_2$ gas or $H_2$—$N_2$ mixed gas prior to the use thereof.

In the process for producing methanol according to the present invention, reaction is carried out by introducing a raw material gas comprising hydrogen and carbon oxides into the catalyst. This reaction is typically carried out at a reaction temperature of 150 to 300° C. under a reaction pressure of 1 to 10 MPa. In the case of the reverse reaction, methanol is decomposed into hydrogen and carbon oxides. The reverse reaction is typically carried out at a reaction temperature of 200 to 400° C. under a reaction pressure of atmospheric pressure to 1 MPa. These reactions can be carried out in any one of a gas phase and a liquid phase. In the reaction in a liquid phase, examples of a solvent used herein are a hydrocarbon type solvent and a solvent non-soluble or insoluble in water.

EXAMPLE

The present invention will be described in more detail with reference to the following examples, but it should not be limited by the examples.

Catalyst Preparation for Methanol Production

Example 1

In 11 kg of distilled water, 5.15 kg (21.3 mol) of copper nitrate 3-hydrate, 3.72 kg (12.5 mol) of zinc nitrate 6-hydrate, 1.25 kg (3.3 mol) of aluminum nitrate 9-hydrate and 0.24 kg (0.8 mol) of colloidal silica (SNOWTEX ST-O® manufactured by NISSAN CHEMICAL INDUSTRIES, LTD., the content of silicic acid anhydride ($SiO_2$) of 20 to 21 wt %) were dissolved, and consequently 21.7 kg of an aqueous solution was prepared as A solution. In this preparation, the molar ratio of Zn to Cu (Zn/Cu) was 0.59 and the molar ratio of Si to Cu (Si/Cu) was 0.038, and the content of copper was 56.2 mol % based on 100 mol % of the total amount of copper, zinc, aluminum and silicon.

Next, in addition to the A solution, 4.58 kg (43.3 mol) of sodium carbonate anhydride was dissolved in 31.2 kg of distilled water and consequently an aqueous solution was prepared as B solution.

The A solution was put into a 100 L precipitation tank equipped with a stirrer and a baffle plate and the B solution was dropped at a rate of about 0.18 L/min with stirring. The feeding time was about 90 min. The liquid temperature in the precipitation tank was set to 20 to 25° C. After the B solution was fed, the pH in the precipitation tank was about 6.2. After the B solution was fed, the temperature of a precipitate slurry was slowly increased to 70° C. and kept for 2 hr. Thereafter, the slurry was washed with pure water until the Na ion concentration in the precipitate was not more than 0.2 mol %, and then filtered off to prepare a precipitate cake. The precipitate cake was dried at 120° C. and calcined at 350° C. to prepare a catalyst for methanol production (Catalyst 1). The resulting catalyst 1 had a specific surface area of 85 $m^2$/g.

Regarding the catalyst 1, the measurement range, the light receiving slit and sampling width in XRD measurement were subjected to the condition (1). The maximum intensity ratio of the peak derived from zinc to the peak derived from copper (ZnO/CuO), as measured by XRD, was 0.22 and the half-value width (2θ) of the peak derived from copper (CuO) was 1.6.

Example 2

The catalyst preparation procedure of Example 1 was repeated except that the usage of colloidal silica (SNOWTEX ST-O® manufactured by NISSAN CHEMICAL INDUSTRIES, LTD., the content of silicic acid anhydride of 20 to 21 wt %) was changed to 0.12 kg, to prepare a catalyst for methanol production (Catalyst 2). In this preparation, the molar ratio of Zn to Cu (Zn/Cu) was 0.59 and the molar ratio of Si to Cu (Si/Cu) was 0.019, and the content of copper was 56.8 mol % based on 100 mol % of the total amount of copper, zinc, aluminum and silicon. The resulting catalyst 2 had a specific surface area of 94 $m^2$/g.

Regarding the catalyst 2, the measurement range, the light receiving slit and sampling width in XRD measurement were subjected to the condition (2). The maximum intensity ratio of the peak derived from zinc to the peak derived from copper (ZnO/CuO), as measured by XRD, was 0.21 and the half-value width (2θ) of the peak derived from copper (CuO) was 1.5.

Example 3

The catalyst preparation procedure of Example 2 was repeated except that the calcination temperature was 450° C., to prepare a catalyst for methanol production (Catalyst 3). The resulting catalyst 3 had a specific surface area of 68 $m^2$/g.

Regarding the catalyst 3, the measurement range, the light receiving slit and sampling width in XPD measurement were subjected to the condition (2). The maximum intensity ratio of the peak derived from zinc to the peak derived from copper (ZnO/CuO), as measured by XRD, was 0.21 and the half-value width (2θ) of the peak derived from copper (CuO) was 1.0.

Comparative Example 1

The catalyst preparation procedure of Example 1 was repeated except that the colloidal silica (SNOWTEX ST-O® manufactured by NISSAN CHEMICAL INDUSTRIES, LTD., the content of silicic acid anhydride ($SiO_2$) of 20 to 21 wt %) was not added, to prepare a catalyst for methanol production (Catalyst 4). In this preparation, the molar ratio of Zn to Cu (Zn/Cu) was 0.59 and the molar ratio of Si to Cu (Si/Cu) was 0.00, and the content of copper was 57.4 mol % based on 100 mol % of the total amount of copper, zinc, aluminum and silicon. The resulting catalyst 4 had a specific surface area of 89 $m^2$/g.

Comparative Example 2

The catalyst preparation procedure of Example 1 was repeated except that the usage of colloidal silica (SNOWTEX ST-O® manufactured by NISSAN CHEMICAL INDUSTRIES, LTD., the content of silicic acid anhydride ($SiO_2$) of 20 to 21 wt %) was changed to 0.36 kg, to prepare a catalyst for methanol production (Catalyst 5). In this preparation, the molar ratio of Zn to Cu (Zn/Cu) was 0.59 and the molar ratio of Si to Cu (Si/Cu) was 0.056, and the content of copper was 55.6 mol % based on 100 mol % of the total amount of copper, zinc, aluminum and silicon. The resulting catalyst 5 had a specific surface area of 86 $m^2$/g.

Comparative Example 3 in distilled water, 5.6 kg of copper nitrate 3-hydrate, 4.1 kg of zinc nitrate 6-hydrate, 1.4 kg of aluminum nitrate 9-hydrate, 2.0 kg of zirconium oxy nitrate 2-hydrate and 0.1 kg of colloidal silica (SNOWTEX ST-O® manufactured by NISSAN CHEMICAL INDUSTRIES, LTD., the content of silicic acid anhydride of 20 to 21 wt %) were dissolved, and consequently 56 L of an aqueous solution was prepared as A solution. In this preparation, the molar ratio of Zn to Cu (Zn/Cu) was 0.59 and the molar ratio of Si to Cu (Si/Cu) was 0.014, and the content of copper was 56.5 mol % based on 100 mol % of the total amount of copper, zinc, aluminum and silicon.

In addition to this, 17.8 kg of sodium carbonate 10-anhydride was dissolved in distilled water and consequently 56 L of an aqueous solution was prepared as B solution.

In a precipitation tank equipped with a stirrer and a baffle plate, 140 L of water was fed and while the stirrer was rotated at 200 rpm, the A solution and the B solution were dropped simultaneously at a rate of about 310 ml/min. The feeding time was 3 hr. The pH of the solution was 7.2±0.2, and the liquid temperature was set to 20 to 25° C.

The temperature of the precipitate slurry was slowly increased to 70° C. and kept for 2 hr. Thereafter, the slurry was washed with pure water until the Na ion concentration in the precipitate was not more than 0.2 mol %. After washing, the precipitate slurry was filtered off to prepare a precipitate cake. The precipitate cake was dried at 120° C. and calcined at 600° C. to prepare a catalyst for methanol production (Catalyst 6). The resulting catalyst 6 had a specific surface area of 85 $m^2/g$.

Regarding the catalyst 6, the measurement range, the light receiving slit and sampling width in XRD measurement were subjected to the condition (1). The maximum intensity ratio of the peak derived from zinc to the peak derived from copper (ZnO/CuO), as measured by XRD, was 0.49 and the half-value width (2θ) of the peak derived from copper (CuO) was 1.3.

Comparative Example 4

The catalyst preparation procedure of Example 2 was repeated except that the calcination temperature was changed to 600° C., to prepare a catalyst for methanol production (Catalyst 7). The resulting catalyst 7 had a specific surface area of 41 $m^2/g$.

Regarding the catalyst 7, the measurement range, the light receiving slit and sampling width in XRD measurement were subjected to the condition (2). The maximum intensity ratio of the peak derived from zinc to the peak derived from copper (ZnO/CuO), as measured by XRD, was 0.24 and the half-value width (2θ) of the peak derived from copper (CuO) was 0.7.

Comparative Example 5

The catalyst preparation procedure of Comparative Example 3 was repeated except that the calcination temperature was changed to 400° C., to prepare a catalyst for methanol production (Catalyst 8). The resulting catalyst 8 had a specific surface area of 136 $m^2/g$.

Figure 2:
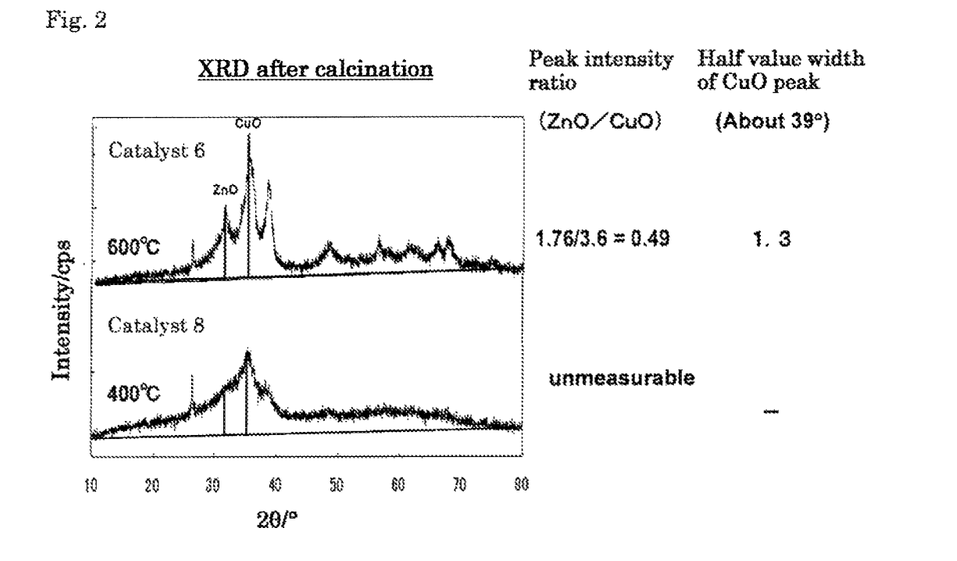
FIG. 2 shows XRD spectra of the catalysts for methanol production prepared in the comparative examples in the present application.

Regarding the catalyst 8, the measurement range, the light receiving slit and sampling width in XRD measurement were subjected to the condition (1). As shown in FIG. 2, clear peaks derived from zinc (ZnO) and copper (CuO) were not observed.

Figure 1:
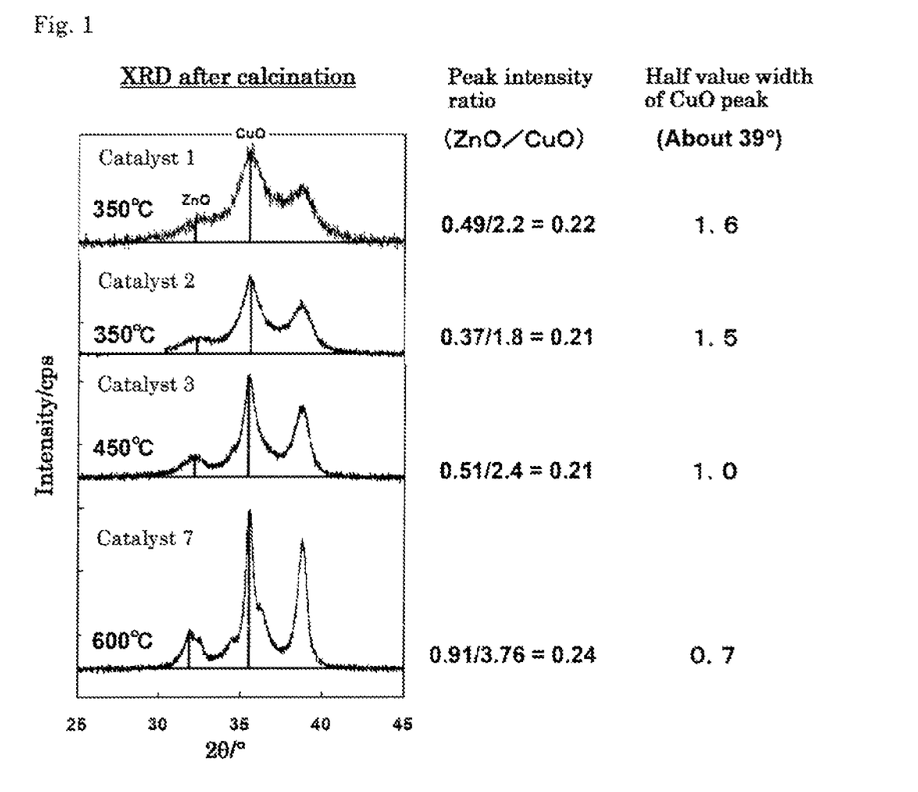
FIG. 1 shows XRD spectra of the catalysts for methanol production prepared in the examples and the comparative examples in the present application.

Regarding the catalysts 1 to 3 prepared in Examples 1 to 3 and the catalyst 7 prepared in Comparative Example 4, the maximum intensity ratio of the peak derived from zinc to the peak derived from copper and the half-value width (2θ) of the peak derived from copper (XRD diffraction curve) are shown in FIG. 1.

Regarding the catalyst 6 prepared in Comparative Example 3 and the catalyst 8 prepared in Comparative Example 5, the maximum intensity ratio of the peak derived from zinc to the peak derived from copper and the half-value width (2θ) of the peak derived from copper (XRD diffraction curve) are shown in FIG. 2.

Production of Methanol

Example 4

[Production of Methanol (Reaction Activity Evaluation)]

Using each of the catalysts 1 and 2 prepared in Examples 1 and 2 and the catalysts 4 to 6 prepared in Comparative Examples 1 to 3, methanol was produced in the following process.

Figure 3:
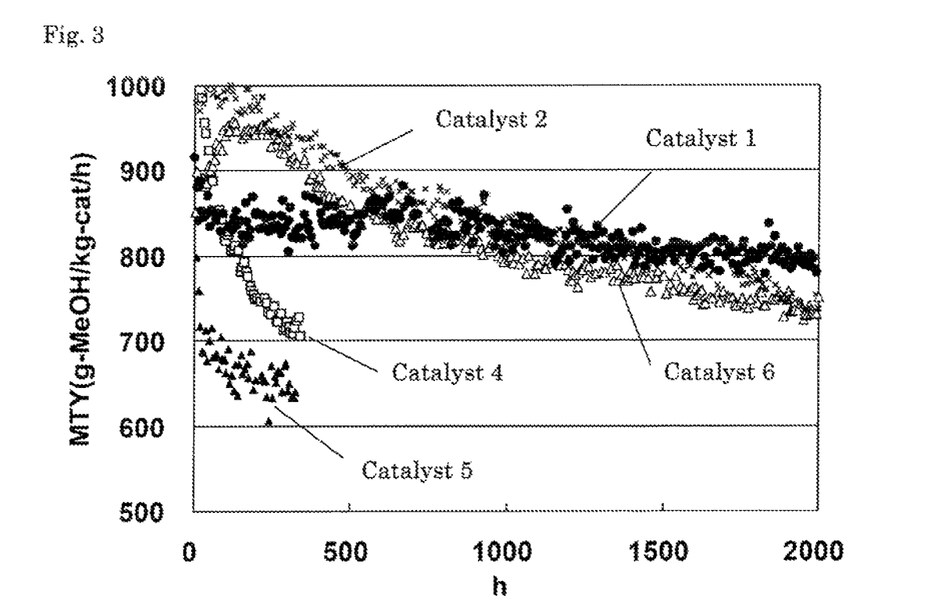
FIG. 3 shows changes with time in the reactions of carbon dioxide and hydrogen in the examples and comparative examples in the present application.

In a reaction tube, 1 ml of the catalyst prepared in the above example was filled and reduced by passing a reducing gas which comprises 10 vol % of $H_2$ and 90 vol % of $N_2$ at 300° C. for 2 hr. Thereafter, the reaction was carried out by passing a mixed gas which comprises 22 vol % of $CO_2$, 3 vol % of CO and 75 vol % of $H_2$ to a catalyst layer at a rate of 30 L/hr at a pressure of 5 MPa at a temperature of 270° C. The reaction formed gas was analyzed by a gas chromatography and the relationship of the reaction time and the methanol yield was determined. The methanol yields (g-MeOH/kg-Cat/hr) are shown in FIG. 3 from the beginning of the reaction to 2000 hr after.

As a result, it was confirmed that the catalyst 1 and the catalyst 2 have high catalyst activity, which is industrially preferable even in continuous operation for a long period of time, and have long time stability. Furthermore, it was also confirmed that the catalyst 4 free from silicon and the catalyst 5 having an excess content of silicon to the copper content have activity which is decreased for a short time and have poor durability. Moreover, it was confirmed that the catalyst 6 which was prepared by calcination at a high temperature and had a high maximum intensity ratio of the peak derived from zinc and the peak derived from copper (ZnO/CuO), as measured by XRD, had insufficient activity after the operation was carried out for 100 hr or more.

The degree of decrease in the reaction rate of each of the catalyst 1 (Example 1) and the catalyst 6 (Comparative Example 3) was determined as a gradient of the decreasing rate of the methanol yield from 1000 h to 2000 h by the least square method. The results are shown in Table 1.

These results indicate that the catalyst 6 in Comparative Example 3 is inferior in long-time stable operating performance as compared with the catalyst 1 in Example 1.

TABLE 1

| Catalyst | Gradient of straight line x (−1 × $10^2$) | $R^2$ |
|---|---|---|
| Catalyst 1 | 3.3 | 0.98 |
| Catalyst 6 | 6.9 | 0.98 |

The invention claimed is:

1. A catalyst for methanol production using carbon oxides as a raw material, which comprises copper, zinc, aluminum and silicon and has the following properties:
   (A) the molar ratio of zinc to copper is 0.5 to 0.7,
   (B) the molar ratio of silicon to copper is 0.015 to 0.05,
   (C) the catalyst comprises CuO and ZnO, and the maximum intensity ratio of a peak derived from the ZnO to a peak derived from the CuO, as measured by XRD, is not more than 0.25 and
   (D) the half-value width (2θ) of a peak derived from the CuO, as measured by XRD, is 0.75 to 2.5.

2. The catalyst for methanol production according to claim 1 wherein the catalyst has a property that (E) the content of zirconium is 0 to 0.1 mol %.

3. The catalyst for methanol production according to claim 1 wherein the content of copper is 45 to 65 mol % provided that the total amount of copper, zinc, aluminum and silicon is 100 mol %.

4. The catalyst for methanol production according to claim 1 wherein the content of an alkali metal is 0 to 0.2 mol %.

5. The catalyst for methanol production according to claim 1 which is obtainable through a step of calcination at a temperature of 300° C. to 450° C.

6. A method for producing the catalyst for methanol production of claim 1, comprising a step of calcination of a catalyst precursor comprising copper, zinc, aluminum and silicon, and having (A) a molar ratio of zinc to copper being 0.5 to 0.7, and (B) a molar ratio of silicon to copper being 0.015 to 0.05, at a temperature of 300° C. to 450° C.

7. A process for producing methanol in the presence of the catalyst for methanol production as claimed in claim 1, carbon oxides and hydrogen.

8. A catalyst for methanol production using carbon oxides as a raw material, which comprises copper, zinc, aluminum and silicon and has the following properties:

(A) the molar ratio of zinc to copper is 0.5 to 0.7, (B) the molar ratio of silicon to copper is 0.015 to 0.05, (C) the maximum intensity ratio of a peak derived from zinc to a peak derived from copper, as measured by XRD, is not more than 0.25 and (D) a powder X-ray diffraction pattern derived from copper comprises a peak at about 39° and the half-value width (2θ) of the peak is 0.75 to 2.5.

9. The catalyst for methanol production according to claim 8 wherein the catalyst has a property that (E) the content of zirconium is 0 to 0.1 mol %.

10. The catalyst for methanol production according to claim 8 wherein the content of copper is 45 to 65 mol % provided that the total amount of copper, zinc, aluminum and silicon is 100 mol %.

11. The catalyst for methanol production according to claim 8 wherein the content of an alkali metal is 0 to 0.2 mol %.

12. The catalyst for methanol production according to claim 8 which is obtainable through a step of calcination at a temperature of 300° C. to 450° C.

13. A method for producing the catalyst of claim 8, comprising a step of calcination of a catalyst precursor comprising copper, zinc, aluminum and silicon, and having (A) a molar ratio of zinc to copper being 0.5 to 0.7, and (B) a molar ratio of silicon to copper being 0.015 to 0.05, at a temperature of 300° C. to 450° C.

14. A process for producing methanol in the presence of the catalyst of claim 8, carbon oxides and hydrogen.

\* \* \* \* \*